US012679796B2

(12) United States Patent　　　　(10) Patent No.:　US 12,679,796 B2
Sugimoto et al.　　　　　　　　　　(45) Date of Patent:　　Jul. 14, 2026

---

(54) HYDROXYALKANOIC ACID CRYSTAL PRODUCTION METHOD AND HYDROXYALKANOIC ACID CRYSTAL POLYMORPH

(71) Applicant: OSAKA GAS CO., LTD., Osaka (JP)

(72) Inventors: Masayuki Sugimoto, Osaka (JP); Jun Tsubota, Osaka (JP); Sae Ishikawa, Osaka (JP)

(73) Assignee: OSAKA GAS CO., LTD., Osaka (JP)

( * ) Notice: Subject to any disclaimer, the term of this patent is extended or adjusted under 35 U.S.C. 154(b) by 526 days.

(21) Appl. No.: 18/257,477

(22) PCT Filed: Dec. 7, 2021

(86) PCT No.: PCT/JP2021/044912
§ 371 (c)(1),
(2) Date: Jun. 14, 2023

(87) PCT Pub. No.: WO2022/131073
PCT Pub. Date: Jun. 23, 2022

(65) Prior Publication Data
US 2024/0101504 A1　　Mar. 28, 2024

(30) Foreign Application Priority Data
Dec. 15, 2020　(JP) ................................. 2020-207383

(51) Int. Cl.
*C07C 51/43*　　　　(2006.01)

(52) U.S. Cl.
CPC .......... *C07C 51/43* (2013.01); *C07B 2200/13* (2013.01)

(58) Field of Classification Search
CPC .. C07C 51/43; C07B 2200/13; C07B 2200/07
See application file for complete search history.

(56) References Cited

U.S. PATENT DOCUMENTS

2017/0327499 A1　11/2017　Ogawa et al.

FOREIGN PATENT DOCUMENTS

| | | | |
|---|---|---|---|
| CN | 110862316 A | 3/2020 | |
| JP | S57026613 A | * 2/1982 | |
| JP | S61205229 A | * 9/1986 | |
| JP | H09510862 A | * 11/1997 | ............... H01S 5/34 |
| JP | 2004509092 A | * 3/2004 | ............. C07C 51/43 |
| JP | 2007536275 A | * 12/2007 | ............... A61P 7/02 |
| JP | 2018000073 A | 1/2018 | |
| WO | 1995007997 A1 | 3/1995 | |

(Continued)

OTHER PUBLICATIONS

Office Action dated Sep. 3, 2024 for corresponding Japanese patent application No. 2020-207383, 24 pages with English translation.

(Continued)

*Primary Examiner* — Deborah D Carr
(74) *Attorney, Agent, or Firm* — MH2 Technology Law Group, LLP

(57)　　　　　　　ABSTRACT

A method for producing a hydroxyalkanoic acid crystal, comprising freeze-drying a solution containing a hydroxyalkanoic acid,
　wherein based on the total amount of the hydroxyalkanoic acid taken as 100 mass %,
　(1) the R form content is 95 to 100 mass % or
　(2) the S form content is 95 to 100 mass %.

6 Claims, 2 Drawing Sheets

(56)     References Cited

FOREIGN PATENT DOCUMENTS

| WO | 2002022546 | A1 | | 3/2002 | | |
| WO | 2005107462 | A2 | | 11/2005 | | |
| WO | WO-2016088863 | A1 | * | 6/2016 | ........... | A61K 9/0019 |

OTHER PUBLICATIONS

International Search Report dated Feb. 22, 2022 for corresponding International Application No. PCTJP2021/044912, 5 pages (with English translation).

* cited by examiner

HYDROXYALKANOIC ACID CRYSTAL PRODUCTION METHOD AND HYDROXYALKANOIC ACID CRYSTAL POLYMORPH

CROSS-REFERENCE TO RELATED APPLICATIONS

This application is a national stage application of PCT/JP2021/044912 filed 7 Dec. 2021 which claims priority to Japanese Patent Application No. 2020-207383 filed 15 Dec. 2020. The entire disclosures of each application are herein incorporated by reference.

TECHNICAL FIELD

The present invention relates to a method for producing a hydroxyalkanoic acid crystal, and a crystalline polymorph of a hydroxyalkanoic acid.

BACKGROUND ART

Hydroxyalkanoic acids typified by 3-hydroxybutyric acid are attracting attention as a breakthrough energy source that can replace carbohydrates. Hydroxyalkanoic acids are not only a mere energy source, but also have excellent effects on cognitive function and long-term continuous memory; thus, they are considered to also be effective for the prevention of Alzheimer's disease.

For example, 3-hydroxybutyric acid (hereinafter also simply referred to as "3HB") is taken up into the blood by ingestion and metabolism of a medium-chain fatty acid (MCT) contained in coconut oil etc., and converted into energy. This process can convert 3HB into energy more quickly than the metabolism of carbohydrates via glycolysis and suppress absorption of fats and sugars into cells. Thus, 3HB is expected to be applied to energy substances for athletes and in the field of diet and health food.

However, 3HB is difficult to handle in its acid state and is commonly provided as a powder in the form of a neutralized salt, such as a sodium salt, a calcium salt, or a magnesium salt.

This is because 3HB does not crystallize easily even when water is removed from an aqueous solution and forms a dimer easily when water is removed, making it difficult to isolate 3HB as a solid.

However, ingestion of a large amount of such a neutralized salt results in excessive salt, which is not desirable for health. Therefore, there is a need for a method for providing hydroxyalkanoic acids, including 3HB, in the form of solid crystals.

Patent Literature 1 discloses a method in which an aqueous solution containing 3HB is subjected to extraction using an organic solvent, concentration under reduced pressure is performed, seed crystals of 3HB are added, and solid crystals of 3HB are obtained using ethyl acetate as a crystallization solvent.

However, this method is not very suitable as a method for obtaining 3HB as a raw material for supplements because the yield of isolated 3HB is not sufficient and an organic solvent is used.

Therefore, there is a need for a method for obtaining a hydroxyalkanoic acid in a high yield.

CITATION LIST

Patent Literature

PTL 1: JP2018-000073A

SUMMARY OF INVENTION

Technical Problem

In view of the above circumstances, an object of the present invention is to provide a method for obtaining solid crystals of a hydroxyalkanoic acid in a high yield.

Solution to Problem

As a result of extensive research to achieve the above object, the present inventors found that a hydroxyalkanoic acid crystal can be produced in a high yield by freeze-drying only a hydroxyalkanoic acid in its R form or a hydroxyalkanoic acid with an extremely high R form content, or only a hydroxyalkanoic acid in its S form or a hydroxyalkanoic acid with an extremely high S form content. The inventors have accomplished the present invention as a result of further research based on this finding.

More specifically, the present invention provides the following methods for producing a hydroxyalkanoic acid crystal.

Item 1.

A method for producing a hydroxyalkanoic acid crystal, comprising freeze-drying a solution containing a hydroxyalkanoic acid, wherein based on the total amount of the hydroxyalkanoic acid taken as 100 mass %, (1) the R form content is 95 to 100 mass % or (2) the S form content is 95 to 100 mass %.

Item 2.

The production method according to Item 1, wherein the solution containing a hydroxyalkanoic acid contains a polar solvent as a solvent.

Item 3.

The production method according to Item 1 or 2, wherein the polar solvent is water.

Item 4.

The production method according to any one of Items 1 to 3, wherein the hydroxyalkanoic acid is 3-hydroxybutyric acid.

Item 5.

A crystalline polymorph of a hydroxyalkanoic acid having diffraction peaks at $2\theta=11.9\pm0.2°$, $12.1\pm0.2°$, $15.0\pm0.2°$, $18.8\pm0.2°$, and $20.9\pm0.2°$ in a powder X-ray diffraction pattern.

Item 6.

The crystalline polymorph according to Item 5, wherein the peak angle I at diffraction angle $2\theta=12.1\pm0.2°$ is the largest.

Item 7.

The crystalline polymorph according to Item 5 or 6, wherein the hydroxyalkanoic acid is 3-hydroxybutyric acid.

Advantageous Effects of Invention

The method for producing a hydroxyalkanoic acid crystal of the present invention enables production of solid crystals of a hydroxyalkanoic acid in a high yield.

DESCRIPTION OF EMBODIMENTS

Figure 1:
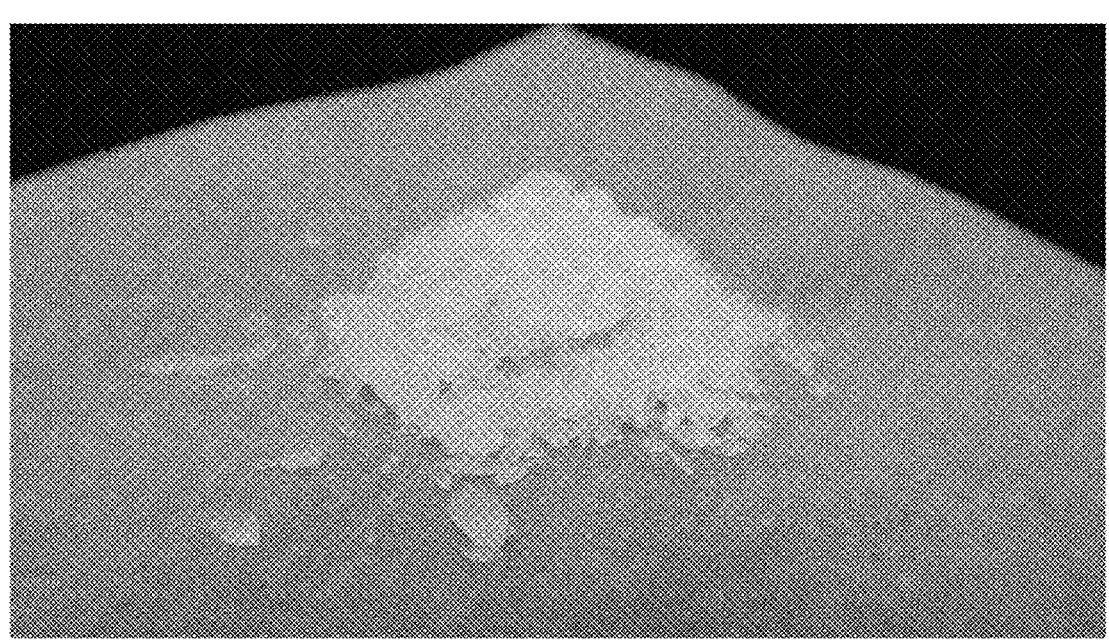
FIG. 1 is a photograph of the 3-hydroxybutyric acid crystals of Example 1.

1. Method for Producing Hydroxyalkanoic Acid Crystal

The method for producing a hydroxyalkanoic acid crystal of the present invention comprises freeze-drying a solution containing a hydroxyalkanoic acid.

Specific examples of the hydroxyalkanoic acid include 3HB, 3-hydroxypentanoic acid, 3-hydroxyhexanoic acid, and lactic acid. Of course, the hydroxyalkanoic acid is not limited to these acids.

Based on the total amount of the hydroxyalkanoic acid contained in the solution taken as 100 mass %, the R form of the hydroxyalkanoic acid is present in an amount of 95 mass % or more, or the S form of the hydroxyalkanoic acid is present in an amount of 95 mass % or more. If the amount of the R form or the S form is less than the lower limit, crystals, which are the final target product, cannot be obtained. Further, the content of the R form or the S form in the total amount of the hydroxyalkanoic acid is preferably 97 mass % or more, and more preferably 99 mass % or more. The upper limits of the R form content and the S form content may be 100 mass %.

The solution containing a hydroxyalkanoic acid may contain substances other than hydroxyalkanoic acids. However, from the viewpoint of obtaining hydroxyalkanoic acid crystals in a high yield and with high purity, the solution is preferably a hydroxyalkanoic acid solution containing only a hydroxyalkanoic acid.

The solvent used in the solution containing a hydroxyalkanoic acid is preferably a polar solvent. Examples of usable polar solvents include known polar solvents, such as aqueous solvents such as water, ether-based solvents such as diethyl ether, tetrahydrofuran, and dioxane, alcohol-based solvents such as ethanol and butanol (preferably t-butanol), and amide-based solvents such as N,N-dimethylformamide and N,N-dimethylacetamide. These solvents may be used singly or in a combination of two or more. In view of the use of hydroxyalkanoic acid crystals, which are the final target product, for supplements and the like, it is preferable to use water and/or ethanol as the polar solvent.

The method for obtaining the solution containing a hydroxyalkanoic acid is not particularly limited, and a wide range of known methods can be used. The solution may be obtained by dissolving a hydroxyalkanoic acid in a solvent or may be obtained by chemical synthesis. The solution containing a hydroxyalkanoic acid may also be obtained by a microbiological method.

In consideration of good production efficiency and reduction of adverse effects of freezing-point depression, the content (concentration) of the hydroxyalkanoic acid in the solution containing a hydroxyalkanoic acid is preferably 1 to 60 mass %, and more preferably 10 to 40 mass %.

In the step of freeze-drying the solution containing a hydroxyalkanoic acid, the temperature and pressure are not particularly limited. The solution may first be frozen at a temperature of preferably −80 to −5° C., more preferably −50 to −20° C., and then freeze-dried at a degree of vacuum of preferably to 110 Pa.

2. Crystalline Polymorph of Hydroxyalkanoic Acid

The present invention includes an invention directed to a method for producing a crystalline polymorph of a hydroxyalkanoic acid.

Specific examples of the hydroxyalkanoic acid include 3HB, 3-hydroxypentanoic acid, 3-hydroxyhexanoic acid, and lactic acid. More specific examples include R-hydroxybutyric acid. Of course, the hydroxyalkanoic acid is not limited to these acids.

The crystalline polymorph of the present invention has diffraction peaks at 2θ=11.9±0.2°, 12.1±0.2°, 15.0±0.2°, 18.8±0.2°, and 20.9±0.2° in a powder X-ray diffraction pattern. It is preferred that among these five peaks, the peak angle I at diffraction angle 2θ=12.1±0.2° is the largest.

Specifically, the powder X-ray diffraction pattern may be measured with a CuKα X-ray tube and at a measurement angle of 5 to 85°.

The crystalline polymorph can be obtained, for example, by the method for producing a hydroxyalkanoic acid described above, and has the advantage of being less deliquescent than conventionally known crystalline forms. For example, when the crystalline polymorph is a crystalline polymorph of 3-hydroxybutyric acid, the crystalline polymorph does not deliquesce even when left in the air for 3 days.

Embodiments of the present invention are described above. However, the present invention is not limited to such embodiments and can, of course, be carried out in various configurations without departing from the gist of the present invention.

EXAMPLES

Embodiments of the present invention are described in more detail below based on Examples. However, the present invention is not limited to these Examples.

Production of Hydroxyalkanoic Acid Aqueous Solution

R-3-hydroxybutyric acid or S-3-hydroxybutyric acid used in the following Examples or Comparative Examples was produced according to the method described in JP2019-176839A. The purity of the obtained R form and the purity of the obtained S form were both 99% ee or more by HPLC measurement.

Example 1

2 g of R-3-hydroxybutyric acid (R-3HB) and 8 g of distilled water were added to a vial, mixed, and heated in a 60° C. water bath to completely dissolve R-3HB. The resulting solution was transferred to a 100-mL flask, completely frozen in a −30° C. freezer, and freeze-dried at a pressure of 110 Pa or less in a room controlled at 25° C. overnight, thereby obtaining R-3HB crystals in a yield of 99% or more (FIG. 1). The freeze dryer used was an FD-1 Freeze Dryer produced by Tokyo Rikakikai Co., Ltd.

Figure 2:
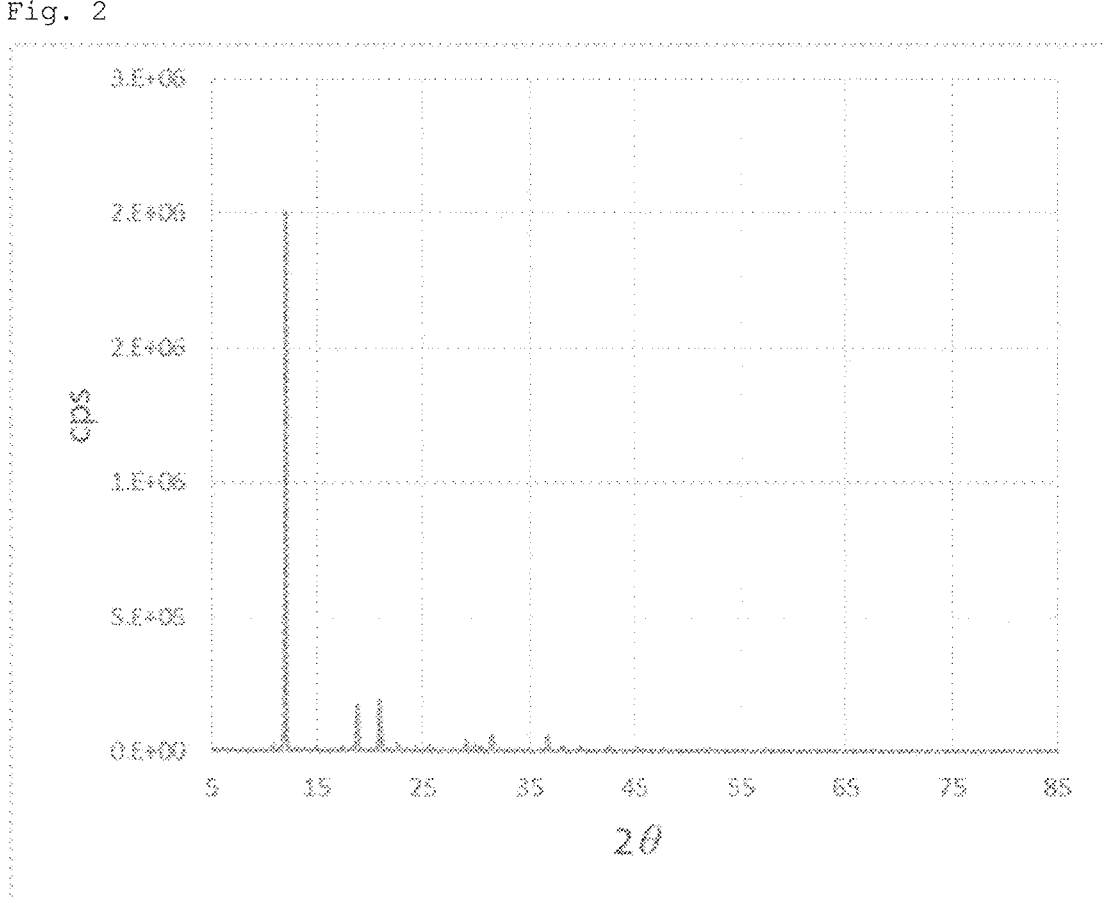
FIG. 2 is a powder X-ray diffraction pattern of the 3-hydroxybutyric acid crystals of Example 1.

An X-ray diffraction pattern of the R-3HB crystals obtained in Example 1 was measured using an X-ray diffraction measurement device (Smart Lab produced by Rigaku) with a CuKα X-ray tube and at a measurement angle of 5 to 85°, and is shown in FIG. 2. In addition, no clear deliquescence was observed after placing 1 g of the crystals on a Petri dish and allowing it to stand in a room at 35 to 40% RH for 3 days, confirming that the crystals obtained in Example 1 are less deliquescent.

Example 2

S-3HB crystals were obtained in a yield of 99% or more in the same manner as in Example 1, except that S-3-hydroxybutyric acid (S-3HB) was used in place of R-3HB.

Example 3

R-3HB crystals were obtained in a yield of 99% or more in the same manner as in Example 1, except that R-3HB was used in an amount of 1 g, and distilled water was used in an amount of 9 g.

Example 4

R-3HB crystals were obtained in a yield of 99% or more in the same manner as in Example 1, except that R-3HB was used in an amount of 3 g, and distilled water was used in an amount of 7 g.

Comparative Example 1

1 g of R-3HB, 1 g of S-3HB, and 8 g distilled water were added to a vial, mixed, and heated in a 60° C. water bath to completely dissolve R-3HB and S-3HB. The resulting solution was transferred to a 100-mL flask, completely frozen in a −30° C. freezer, and freeze-dried at a pressure of 110 Pa or less in a room controlled at 25° C. overnight. No crystallization occurred, and the solution remained liquid.

Comparative Example 2

5 g of R-3HB and 1.5 g of ethyl acetate were added to a vial, mixed, and heated in a 60° C. water bath to completely dissolve R-3HB. The resulting solution was allowed to return to room temperature, and one seed crystal of R-3HB was added. The resulting mixture was allowed to stand in a 4° C. refrigerator overnight to precipitate R-3HB crystals. The R-3HB crystals were isolated by filtration and weighed, and the yield was about 60%.

Comparative Example 3

100 mL of an aqueous solution containing 10 mass % R-3HB was concentrated using an evaporator at a temperature of 70° C. until no water was released. High-performance liquid chromatography (HPLC) revealed that the concentrate contained about 8% 3HB dimer in terms of area ratio. Seed crystals of R-3HB were added to the concentrate; however, the concentrate did not crystallize completely and was in a semi-solid state. The HPLC measurement was performed using a Chromaster (produced by Hitachi High-Tech Science Corporation) equipped with a MetaCarb 67H column (produced by Agilent), a 2.5 mmol/L sulfuric acid aqueous solution as the mobile phase, and an RI detector.

The invention claimed is:

1. A method for producing a 3-hydroxybutyric acid crystal, comprising freeze-drying a solution containing 3-hydroxybutyric acid,
    wherein based on the total amount of the 3-hydroxybutyric acid taken as 100 mass %,
        (1) the R form content is 95 to 100 mass % or
        (2) the S form content is 95 to 100 mass %.

2. The production method according to claim 1, wherein the solution containing 3-hydroxybutyric acid contains a polar solvent as a solvent.

3. The production method according to claim 1, wherein the polar solvent is water.

4. A crystalline polymorph of 3-hydroxybutyric acid having diffraction peaks at 2θ=11.9+0.2°, 12.1+0.2°, 15.0+0.2°, 18.8+0.2°, and 20.9+0.2° in a powder X-ray diffraction pattern.

5. The crystalline polymorph according to claim 4, wherein the peak angle I at diffraction angle 2θ=12.1+0.2° is the largest.

6. The production method according to claim 2, wherein the polar solvent is water.

* * * * *